United States Patent [19]
Slater et al.

[11] Patent Number: 6,039,211
[45] Date of Patent: Mar. 21, 2000

[54] POSITION TRIGGERED DISPENSER AND METHODS

[75] Inventors: Joseph A. Slater; Sam Chan, both of San Jose, Calif.

[73] Assignee: Glaxo Wellcome Inc., Research Triangle Park, N.C.

[21] Appl. No.: 09/158,326

[22] Filed: Sep. 22, 1998

[51] Int. Cl.[7] .................................................. G01F 11/00
[52] U.S. Cl. ...................... 222/1; 222/137; 222/402.24; 141/1; 141/130; 73/863.32; 422/101; 422/102
[58] Field of Search .................................. 141/1, 94, 156, 141/157, 159, 160, 130, 129, 178, 237, 238, 242, 244; 422/65, 100, 101, 102; 73/863.1, 863.32; 222/1, 137, 402.24

[56] References Cited

U.S. PATENT DOCUMENTS

| | | | |
|---|---|---|---|
| 3,188,181 | 6/1965 | Peterson et al. | 141/130 |
| 3,261,208 | 7/1966 | Fisher | 73/863.32 |
| 3,837,534 | 9/1974 | Natelson | 222/137 |
| 3,951,605 | 4/1976 | Natelson | 141/130 |
| 4,478,094 | 10/1984 | Salomaa et al. | 73/863.32 |
| 4,875,605 | 10/1989 | Weston | 222/402.24 |
| 4,944,922 | 7/1990 | Hayashi | 422/100 |
| 5,411,065 | 5/1995 | Meador et al. | 141/130 |
| 5,759,494 | 6/1998 | Szlosek | 422/102 |
| 5,939,024 | 8/1999 | Robertson | 422/101 |

*Primary Examiner*—Steven O. Douglas
*Assistant Examiner*—Khoa Huynh
*Attorney, Agent, or Firm*—Darin J. Gibby; Lauren L. Stevens

[57] ABSTRACT

The invention provides systems, methods, and apparatus for dispensing liquids. According to one method, a plate is provided having a plurality of wells. At least one marker is also provided and is associated with at least some of the wells. The plate and marker are moved relative to a plurality of liquid dispensing elements, and the presence of the marker is sensed with a sensor that is disposed at a known location relative to the dispensing elements. The sensing of the marker indicates that at least some of the wells are aligned with the dispensing elements. As such, liquid is dispensed from the dispensing elements and into the aligned wells after sensing the presence of the marker.

36 Claims, 6 Drawing Sheets

POSITION TRIGGERED DISPENSER AND METHODS

BACKGROUND OF THE INVENTION

The invention relates generally to the field of liquid dispensing, and in particular to the dispensing of liquids into relatively small wells. More specifically, the invention provides systems and methods for rapidly filling ells of multi-well plates with precise volumes of liquids.

In various fields of chemical and biological research, there is a need to place known volumes of liquids within wells to facilitate the performance of various procedures. One common procedure is the performance of assays where various chemicals or substances are introduced into the wells and any reactions are evaluated. As another example, synthesized chemical compounds which have been cleaved from solid supports are typically transferred to sample wells for analysis. Various liquids are introduced into the wells to assist in identifying a particular compound as generally known in the art.

The wells which receive the liquids are often formed in plates in a standard arrangement or format. For example, one common format is a 96 well format where the plate is generally rectangular in geometry and has its wells arranged in eight rows and twelve columns. Such multi-well plates are well known within the art and are available from a host of commercial supplies, such as Polyfiltronics. The use of standard sized plates is advantageous because such plates may be used with most commercially available handling and processing equipment. For example, most automated plate readers, some speed vacuum concentrators, autosamplers, robotics liquid handling equipment, and the like, are configured to operate with standard multi-well plate formats.

One common way to introduce liquids into the wells of such plates is to use a multi-channel air-displacement pipette. For example, when using a 96 well plate, multi-channel pipettes with eight tips are available to simultaneously fill an entire one of the columns with the same liquid. To fill the wells, the user manually places the array of pipette tips into a liquid source to aspirate the liquid into the pipettes. The user then places the array of pipette tips into one of the columns of wells and squeezes a plunger to force an amount of liquid out of the pipettes and into the wells.

Such a process suffers from a number of drawbacks. For example, such manual transfer of the liquid is burdensome and time consuming. Further, certain fluids, such as those with high vapor pressures at room temperature, tend to be difficult to dispense with such air-displacement pipettes since the pressure in the pipette tips often forces out droplets of the fluid even before dispensing is desired. This causes both inaccuracies in dispensing and placement of fluid in unwanted locations on the plate. Such a deficiency is particularly troublesome when dispensing highly corrosive or otherwise hazardous liquids, such as trifluoroacedic acid (TFA).

Automated systems for dispensing fluids into multi-well plates are widely available. Typically, such systems are not constructed of materials that are compatible with highly corrosive materials. In addition, many of these systems are large compared with chemical vapor hoods which are typically used in chemistry laboratories and which are required when using hazardous liquids like TFA.

Hence, it would be desirable to provide improved apparatus, systems, and methods for transferring liquids into wells of multi-well plates that would overcome or greatly reduce the drawbacks associated with prior art techniques. In particular, it would be desirable to provide ways to rapidly and efficiently fill the wells with the desired liquids. Further, such systems and methods should be safe to ensure that hazardous chemicals are properly transferred and should be small enough to be placed in conventional chemical vapor hoods. Still further, the systems and methods should allow for precise volumes of liquids to be transferred into the wells.

SUMMARY OF THE INVENTION

The invention provides exemplary methods, systems, and apparatus for dispensing liquids. According to the invention, the liquids are dispensed into a plurality of wells included in a multiwell plate. In one exemplary method, at least one marker is associated with at least some of the wells. The plate and the marker are moved relative to a plurality of liquid dispensing elements that are employed to dispense a liquid into the wells. The presence of the marker is sensed with a sensor that is disposed at a known location relative to the dispensing elements. The sensing of the marker indicates that at least some of the wells are aligned with the dispensing elements. As such, the liquid is dispensed from the dispensing elements and into the aligned wells after the presence of the marker has been sensed. In this way, the wells of the plate may be filled simply by moving the plate and the associated marker relative to the dispensing elements to position the wells beneath the dispensing elements. The sensing of the marker indicates proper alignment so that the wells may automatically be filled.

In one exemplary aspect, the marker is included on a carrier which is configured to removably hold the plate. In this way, the plate is simply placed onto the carrier such that the wells are at a known location relative to the marker. The carrier is then translated to move the plate beneath the dispensing elements. In this manner, essentially any type of plate, and particularly standard off-the-shelf multi-well plates, may be used with the invention simply by placing them onto the carrier which includes the marker. Alternatively, the marker may be included on the plate itself.

In another aspect, the wells are disposed in rows in the plate, and a separate marker is associated with each row. In this way, each successive row may be filled with liquid by moving the plate until each marker is sensed. When each marker is sensed, liquid is dispensed through the dispensing elements and into the associated row.

In another aspect of the method, either the same liquid or a different liquid may be dispensed from each of the dispensing elements. In this way, the wells may all be filled with the same or a different liquid. In still another aspect, the volume of liquid dispensed into the aligned wells is precisely controlled. This can be done, for example, by controlling the flow rate and the time for which liquid is dispensed through the dispensing elements.

In yet another aspect, the fluid is under pressure and a valve which is positioned between the pressurized liquid and the dispensing elements is opened after the presence of the marker has been sensed. As the valve is opened, the liquid is forced from the dispensing elements and into the aligned wells.

The sensor is preferably configured to sense a change in reflectively as the sensor passes over the marker. For example, the marker may comprise a darkened region which reflects less light than surrounding regions. Alternatively, the sensor may be disposed on a side of the marker opposite of a light source and employed to detect the passage or blockage of light due to the presence of the marker. For example, the marker may comprises an opaque region. As the opaque region moves over the sensor, the sensor detects the blockage of light. Alternatively, the marker may comprise a transparent region, with the sensor sensing the transmission of light through the transparent region.

The invention further provides an exemplary liquid dispensing system for use with a plate having a plurality of wells. The system includes a carrier having at least one marker and a region for receiving the plate. At least one source of liquid is provided, and a plurality of liquid dispensing elements are coupled to the source of liquid. A sensor is disposed to sense the presence of the marker when at least some of the wells are aligned with the dispensing elements. A controller is also included to dispense liquid from the dispensing elements upon receipt of a signal from the sensor which indicates that the marker has been sensed and that at least some of the wells are aligned with the dispensing elements.

In one aspect, the system further includes a base having at least one track along which the carrier is moved. In this way, lateral movement of the plate is prevented so that the wells remain laterally aligned with the dispensing elements. More than one track may be included on the base to allow for lateral variability. For example, if the plate has more wells per row than there are dispensing elements in the system, the carrier may be moved to another track to allow another set of wells in the row to be filled.

The source of liquid is preferably placed under pressure, and at least one valve is coupled to the source of liquid. In this way, the controller is configured to open the valve upon receipt of the signal from the sensor to allow the liquid to be dispensed through the dispensing elements. Preferably, the controller comprises a relay which sends a signal to open the valve upon receipt of the signal from the sensor. In another aspect, the controller is configured to control the volume of liquid dispensed from each dispensing element. This may be accomplished, for example, by controlling the amount of time that the valve is opened and by controlling the flow rate of the liquid through the dispensing elements.

In one alternative, a manifold is coupled to the dispensing elements so that the same liquid may be dispensed from each of the elements upon opening of the valve. In another alternative, each of the dispensing elements is coupled to a separate source of liquid, with each source having its own valve. In this way, different liquids may be introduced into the wells upon opening of the valves by the controller.

In one particular aspect, the marker comprises a darkened region, and the sensor is configured to sense a change in reflectance of light as the sensor passes over the marker. Alteratively, the marker may comprise a transparent region, and a light source is provided to project light through the region when the wells are aligned with the dispensing elements. Alternatively, the marker may comprise an opaque region, with the light source projecting light onto the sensor until blocked by the marker when the wells are aligned with the dispensing elements. In yet another aspect, the wells are preferably disposed in rows, and a separate marker is associated with each row so that liquid will be dispensed into each row as the plate is advanced relative to the dispensing elements.

DETAILED DESCRIPTION OF THE SPECIFIC EMBODIMENT

The invention provides exemplary methods, systems, and apparatus for the controlled dispensing of liquids. According to the invention, the liquids are dispensed into the wells of a multi-well plate. Such plates can be formatted with essentially any format and have any number of wells. One particularly useful type of plate is a standard 96 multiwell plate. However, it will be appreciated that other types of plates may be employed, including 864 well plates, and other standard plates as they become available. As described hereinafter, the invention may be used with essentially any off-the-shelf multi-well plate. Alternatively, the invention may be used with multi-well plates which have been modified to include one or more markers.

Dispensing of the liquids into the wells is preferably accomplished by the use of dispensing elements that are aligned with the wells. Such dispensing elements may comprise, for example, tubular members through which the liquids may be dispensed. As one example, the tubular members may be fashioned in the form of individual pipettes as is known in the art. The dispensing elements may be arranged in any systematic manner so that a predetermined number of the wells will be filled each time liquids are dispensed through the dispensing elements. For example, the dispensing elements may be arranged in a linear array so that they will fill an entire row, or a part of a row, of wells. Alternatively, the dispensing elements may be arranged in a two dimensional array so that two or more rows of wells, or all of the wells of the plate, may be filled at a time.

To determine when the dispensing elements are aligned with the appropriate wells, one or more sensors is employed to detect one or more markers on or associated with the plate. For instance, the markers are preferably disposed either on a carrier which holds the plate or on the plate itself in a manner such that each marker is associated with a predetermined arrangement of wells. For example, each row of wells may be aligned with a separate marker. Alternatively, the markers may be offset from each of the row of wells. The sensors are then employed to detect each marker. As a marker is detected, liquid is dispensed through the dispensing elements so that they will fill the wells that are associated with the sensed marker. As the plate is advanced relative to the sensor, another marker is sensed and another set of wells is filled in a similar manner.

A wide variety of sensors may be employed to detect the presence of the markers. Preferably the sensor will comprise an optical sensor that detects a change in reflectance of light, the passage of light or the absence of light to indicate that the marker has been sensed. Alternatively, mechanical sensors may be employed to sense markers which are configured as detents, bumps, ridges, or the like, that are disposed on the carrier or the plate. In another alternative, an ultrasound sensor may be employed to detect the presence of an ultrasonically opaque mark on the carrier or the plate. As a further embodiment, the sensor may comprise an electrical circuit that is either opened or closed as the marker moves out of or into the electrical circuit.

The invention may be configured to dispense a wide variety of liquids into the wells. Merely by way of example, various chemicals and/or substances may be introduced into the wells to facilitate the performance of assays. Liquids employed to identify a particular compound that was produced using a chemical synthesis process may also be employed. Still further, chemicals used to perform a chemical synthesis process may also be used. Such chemicals can include, for example, reagents, buffer solutions, washing solutions, and the like. The invention is particularly advantageous in dispensing corrosive or hazardous chemicals by precisely transferring the liquids into the wells with minimal or no spillage. One exemplary chemical that may be dispensed by the invention is TFA. The system of the invention may also be constructed to be small enough that it will fit within a standard chemical vapor hood as is known in the art.

When filling the wells, the invention may be configured such that each of the dispensing elements dispenses the same type of liquid. Alternatively, some of the dispensing elements may dispense other kinds of liquids so that a variety of liquids are placed in the wells of the plate. Further, the invention is preferably configured so that a precise volume of the liquid is transferred to each of the wells. An exemplary way to control the volume of the liquids dispensed is by controlling the rate of the flow through the dispensing elements and the time during which the liquid is transferred through the dispensing elements.

Figure 1:
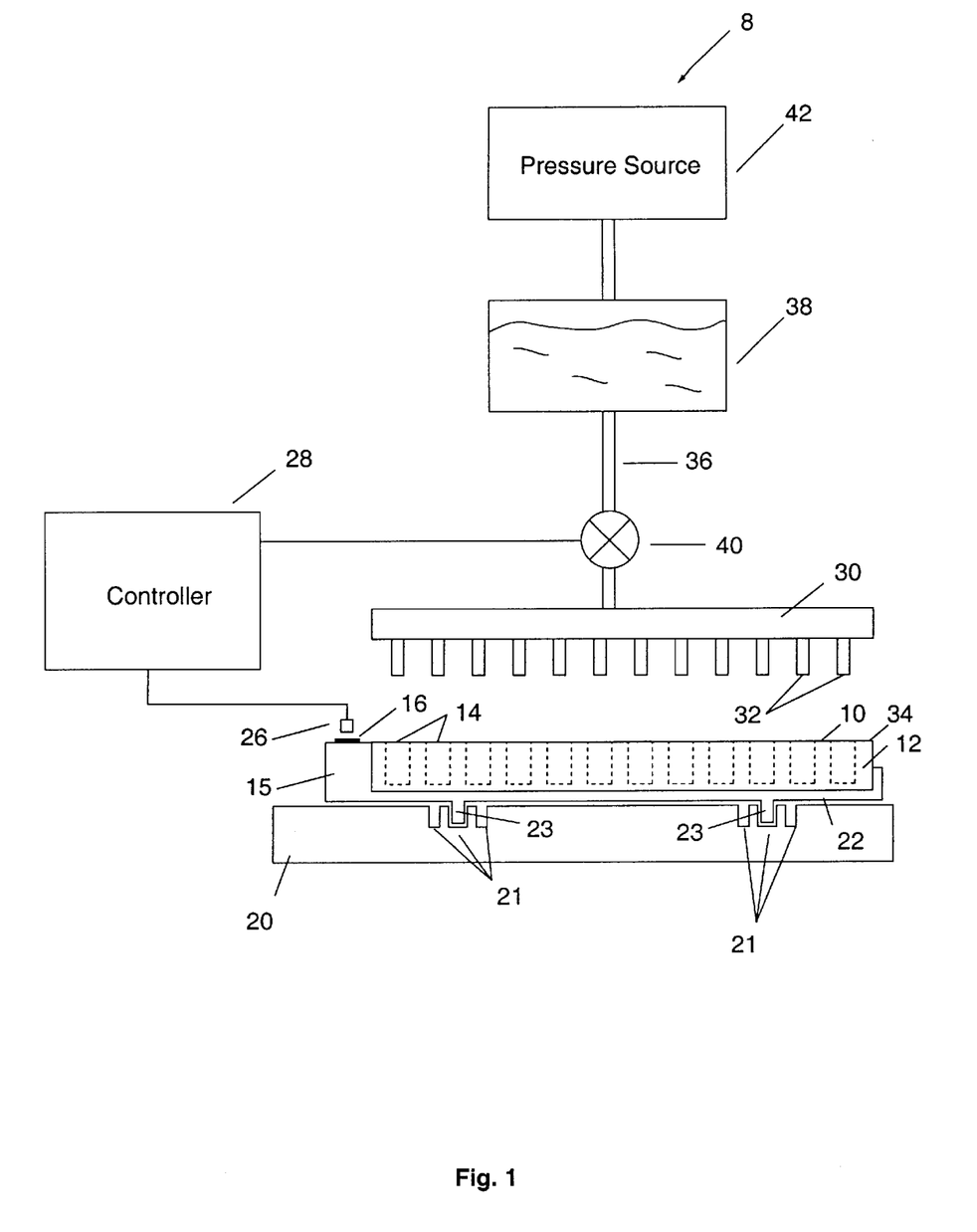
FIG. 1 is a side schematic view of an exemplary liquid dispensing system according to the invention.
Figure 2:
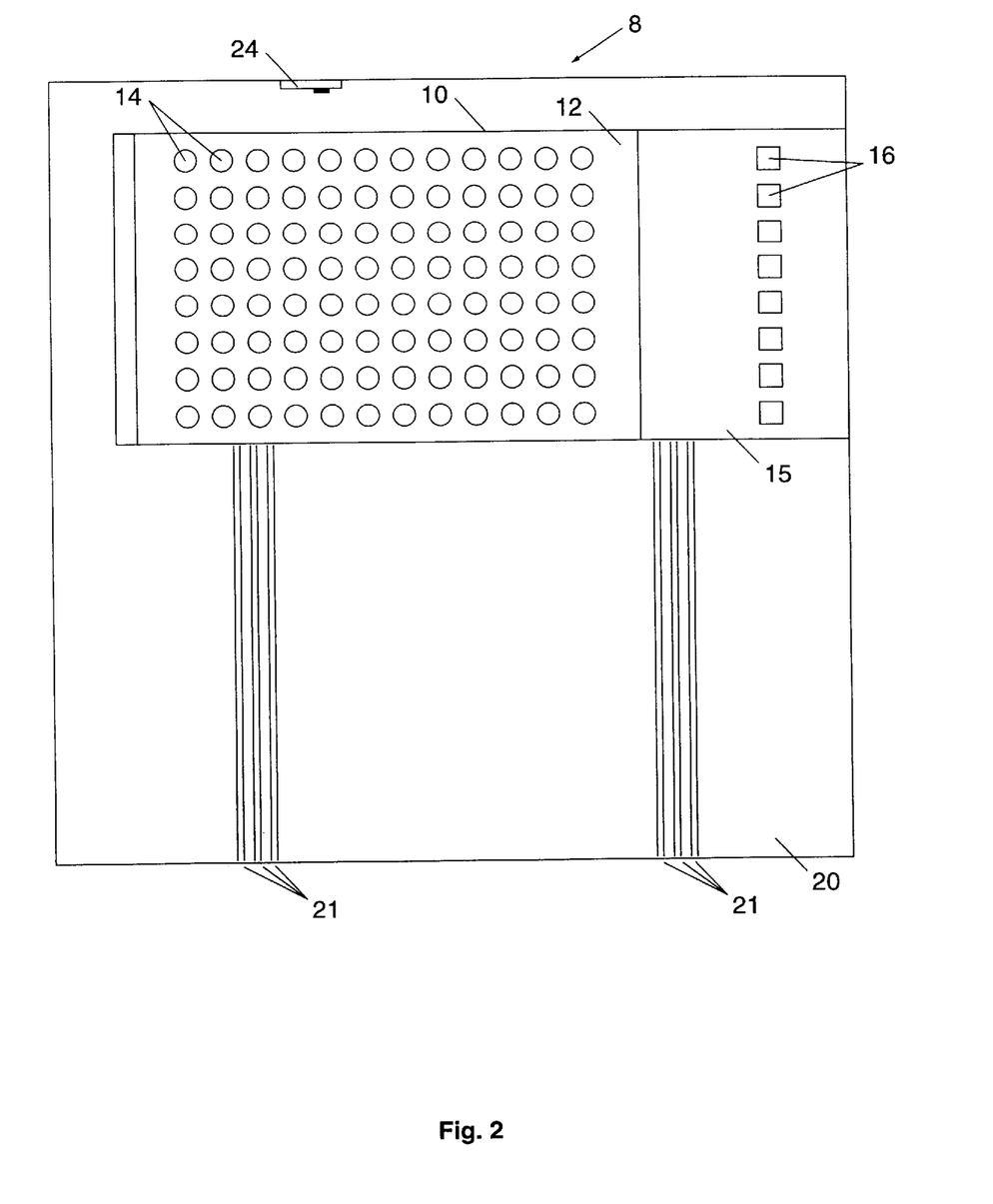
FIG. 2 is a top view of a base, a carrier, and a multi-well plate of the system of FIG. 1.

Referring now to FIGS. 1 and 2, an exemplary embodiment of a liquid dispensing system 8 will be described. System 8 is operated using a multiwell plate 10. Plate 10 comprises a plate body 12 having formed therein a plurality of wells 14. As shown, the wells are arranged in rows and columns in a standard 96 well format. However, it will be appreciated that system 8 may be used with essentially any type of standard well format, including 864 well plates and the like. As such, the volume of wells 14 may vary depending on the particular use, with preferable volumes being in the range from about 1 $\mu L$ to about 5 mL, and most preferably from about 5 $\mu L$ to about 200 $\mu L$. Conveniently, body 12 may be constructed of a plastic material, with wells 14 being formed in body 12 using a molding process as is known in the art.

System 8 includes a carrier 15 to hold plate 10. Included on carrier 15 are a plurality of markers 16. Conveniently, markers 16 may be included on a marker strip so that a different arrangement of markers may be provided simply by removing the strip and replacing it with another strip having a different arrangement of markers. In this way, carrier 15 may easily be modified to accommodate plates having different numbers and/or arrangements of wells. Alternatively, markers 16 may be stamped or painted onto carrier 15 or may be integrally formed therein. As shown, markers 16 are aligned with each of row of wells 14. In this way, each row of wells may be filled with liquid upon sensing the aligned marker 16 as described in greater detail hereinafter. However, it will be appreciated that other arrangements of markers 16 may be provided. For example, marker 16 may be offset from each of the rows. Further, one marker may be associated with two or more rows of wells.

System 8 further includes a base 20 for receiving carrier 15. Base 20 includes three pairs of tracks 21. At a bottom 22 of carrier 15 are a pair of rails 23 which may be placed into any one of the three pairs of tracks 21 (it being appreciated that any number of tracks may be included in base 20). Disposed above plate 10 is a sensor 26. Under either normal or enhanced lighting, the light reflected from carrier 15 and sensed by sensor 26 will vary depending on whether sensor 26 is over one of markers 16. Markers 16 preferably comprise darkened regions which are surrounded by lighter regions. When sensor 26 passes over one of markers 16, it detects the change in reflectance. Sensor 26 is then configured to send a signal to a controller 28 indicating the presence of one of markers 16. An exemplary sensor 26 that may be employed to detect the change in reflectance comprises an optical sensor, part # EESPZ301Y01, commercially available from Omron. Sensor 26 is preferably positioned about 3 mm above carrier 15.

Disposed above plate 10 is a manifold 30 to which is coupled a plurality of dispensing elements 32. Dispensing elements 32 are formed in a linear array. Tracks 21 prevent lateral movement of carrier 15 so that wells 14 will be laterally aligned with dispensing elements 32 as carrier 15 is moved under dispensing elements 32. As shown, dispensing elements correspond in number to the number of wells 14 of any given row. More specifically, system 10 is shown to include twelve dispensing elements 32, which correspond to the twelve wells in each of the rows of wells in plate 10. Tracks 21 make it possible for dispensing elements 32 to fill rows having more than twelve wells. For example, by providing three sets of tracks 21 (which are about 3 mm apart), plate 10 may be moved to three different lateral positions so that the twelve dispensing elements 32 may fill the 36 rows of wells in an 864 well plate. For 96 well plates, rails 23 of carrier 15 preferably remain in the center set of tracks 21.

When using a plate with a different number of wells, such as, for example, an 864 well plate, markers 16 will need to be changed. For example, with an 864 well plate, the eight markers having a 9 mm spacing are changed to 24 markers having a 3 mm spacing. Conveniently, markers 16 may be formed in a teflon coated metal strip which is removed and replaced with a different arrangement of markers depending on the type of plate to be used.

As best shown in FIG. 2, base 20 includes a stop 24 to prevent translation of carrier 15 beyond the last row of wells 14. Further, stop 24 includes a sensor, such as a mechanical switch, which sends a signal to controller 28 which disables further dispensing. In this way, plate 10 may be moved back to the starting position without dispensing occurring. When another plate is ready to receive liquid, the user actuates an "enable" switch on controller 28 to reset the system.

Dispensing elements 32 are preferably spaced apart from a top 34 of plate 10 by a distance sufficient to ensure that substantially all of the liquid dispensed through dispensing element 32 will be transferred into wells 14. Dispensing element 32 are preferably tubular in geometry, with the fluid passages having a diameter that is smaller than that of wells 14.

Coupled to manifold 30 by a line 36 is a source of liquid 38. Disposed in line 36 is a valve 40 which is employed to control the flow of liquid from source 38 into manifold 30. Liquid source 38 is preferably placed under pressure using a pressure source 42 which includes a pressurized gas. In this way, when valve 40 is opened, liquid is forced into manifold 30 and through dispensing elements 32. Valve 40 is also coupled to controller 28. In this way, opening and closing of value 40 may be controlled by controller 28. In this manner, when controller 28 receives a signal from sensor 26 indicating the presence of one of markers 16, controller 28 sends a signal to valve 40 to cause valve 40 to open and to allow fluid to flow into manifold 30 and out of dispensing elements 32 where it is transferred to wells 14. Use of the pressurized liquid is particularly advantageous in that liquids with high vapor pressures, such as TFA, may be dispensed without prematurely leaking from dispensing elements 32.

Controller 28 preferably comprises a timer relay which causes valve 40 to open for a predetermined amount of time upon receipt of a signal from sensor 26. The time setting is preferably adjustable to vary the length of time that valve 40 is opened and thereby control the volume of liquid transferred into the wells. Valve 40 preferably comprises an inert solenoid valve, with actuation of the solenoid being controlled by controller 28.

Figure 3:
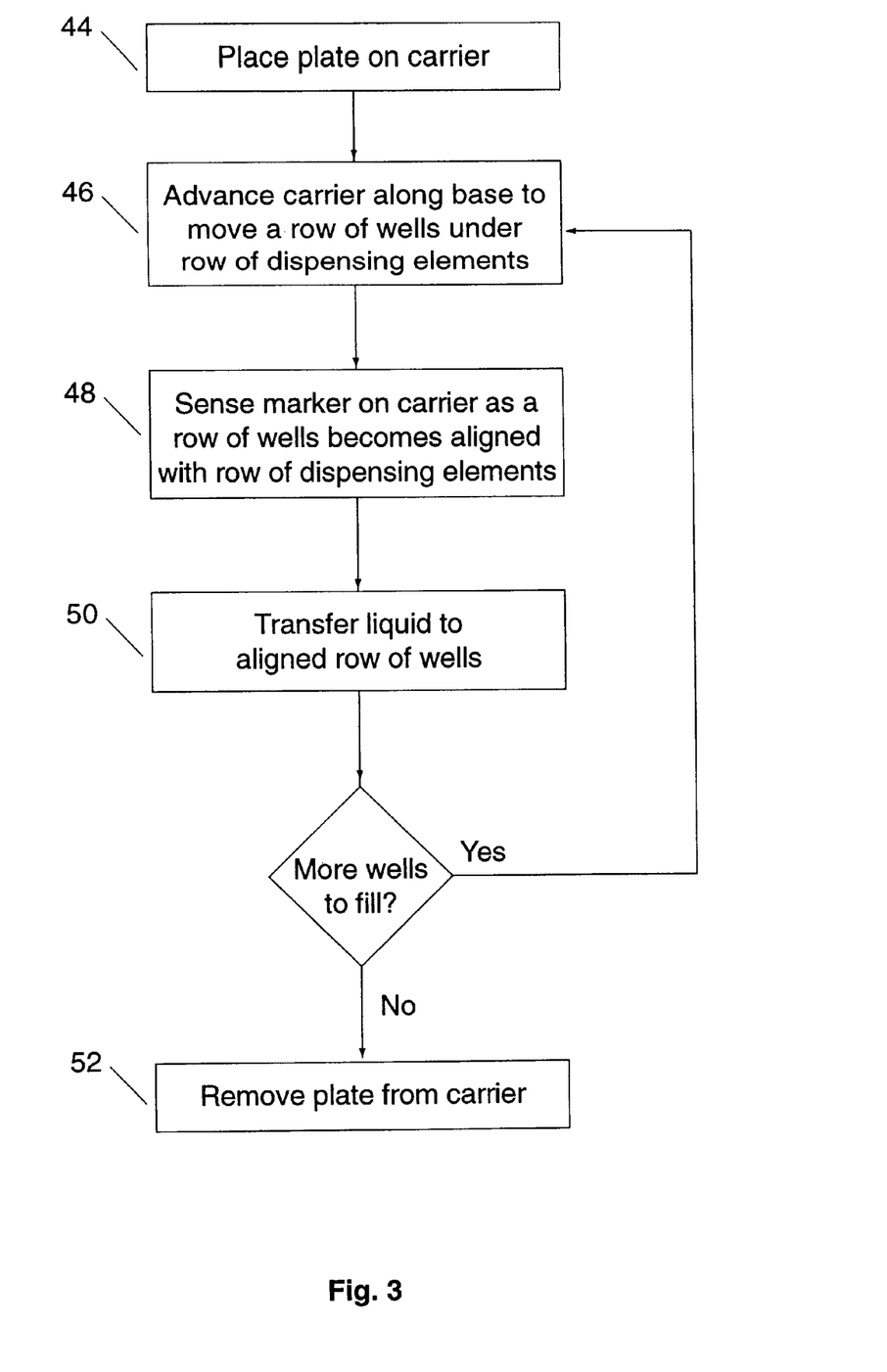
FIG. 3 is a flow chart illustrating an exemplary method for dispensing liquids according to the invention.

Referring now to FIG. 3, an exemplary method for operating system 10 will be described. Initially, plate 10 is placed on carrier 15 as illustrated in step 44. Carrier 15 is then advanced along tracks 21 in a direction generally perpendicular to a plane passing through dispensing elements 32 to position a first row of wells 14 beneath dispensing elements 32, as illustrated in step 46.

As the first row of wells 14 becomes aligned with dispensing elements 32, marker 16 is detected by sensor 26 as illustrated in step 48. In turn, sensor 26 sends a signal to controller 28 which causes valve 40 to open to allow liquids from source 38 to be dispensed into the aligned row of wells 14 as illustrated in step 50. As previously described, controller 28 is configured to control the amount of time that valve 40 is opened to control the volume of liquid dispensed. The amount of pressure supplied by source 42 is also controlled to control the volume of liquid dispensed.

If more rows are to be filled with liquid, plate 10 is further advanced until the next marker 16 is sensed and another row of wells is filled with liquid in a manner similar to that previously described. Plate 10 may be advanced manually or by the use of an automated translation mechanism. Once all of the desired rows are filled, carrier 15 engages stop 24 to disable dispensing. Carrier is then withdrawn and plate 10 may be removed as illustrated in step 52.

Figure 4:
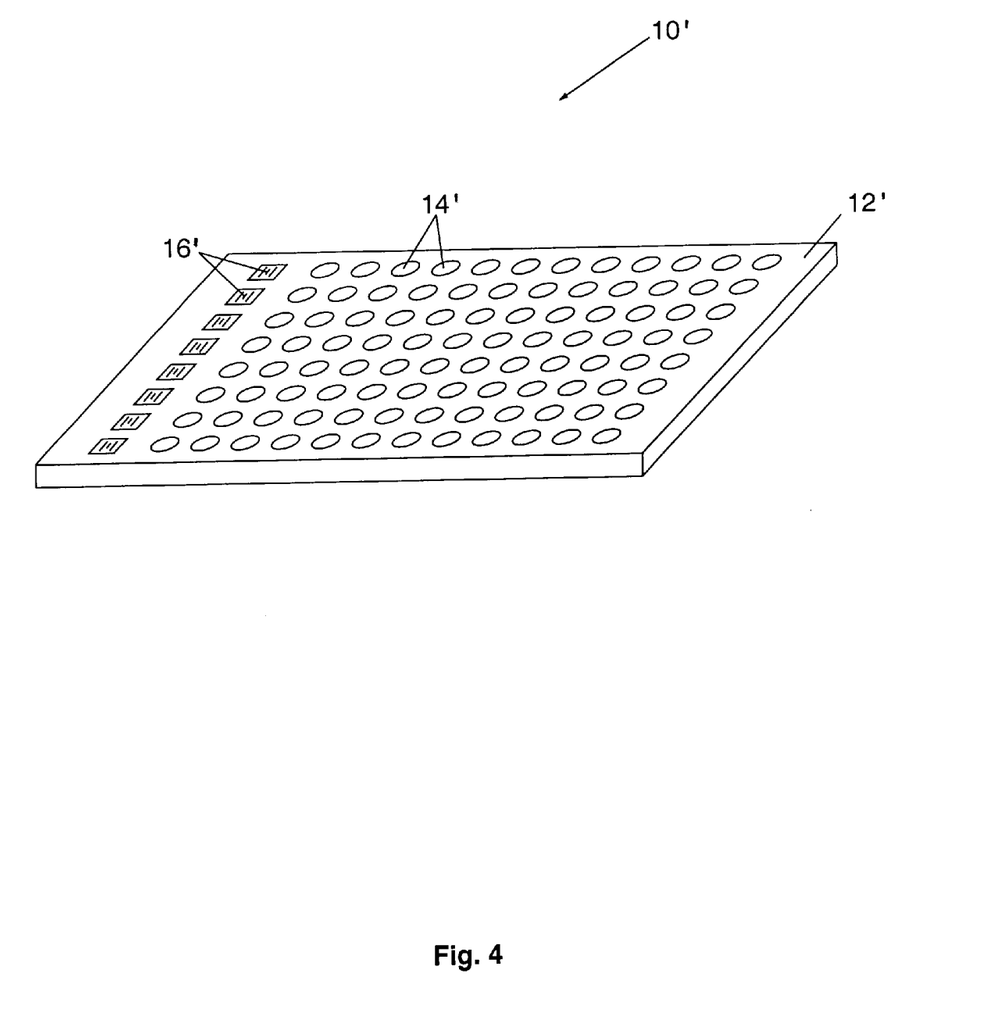
FIG. 4 is a perspective view of an alternative plate having a plurality of wells and a marker that is aligned with each row of wells according to the invention.

Although plate 10 is shown as being used with carrier 15, it will be appreciated that plate 10 may be modified to include markers so that carrier 15 need not be employed. For example, as illustrated in FIG. 4, plate 10 has been modified and is referred to as plate 10'. Plate 10' comprises a plate body 12' having a plurality of wells 14'. A plurality of markers 16' are disposed on plate 10'. Plate body 12' may also include rails to slide along tracks 21 of base 20. With this configuration, markers 16' may be sensed as plate 10' is translated along tracks 21 to allow liquid to be dispensed in a manner similar to that previously described.

As an alternative to sensing a change in reflectance, the system of the invention may sense the passage of light through a transparent marker or the blockage of light by an opaque marker. For example, plate 10' (or carrier 15) may be constructed to be transparent to light and include opaque markers. In this way, the markers block light from directly impinging on a sensor.

Figure 5:
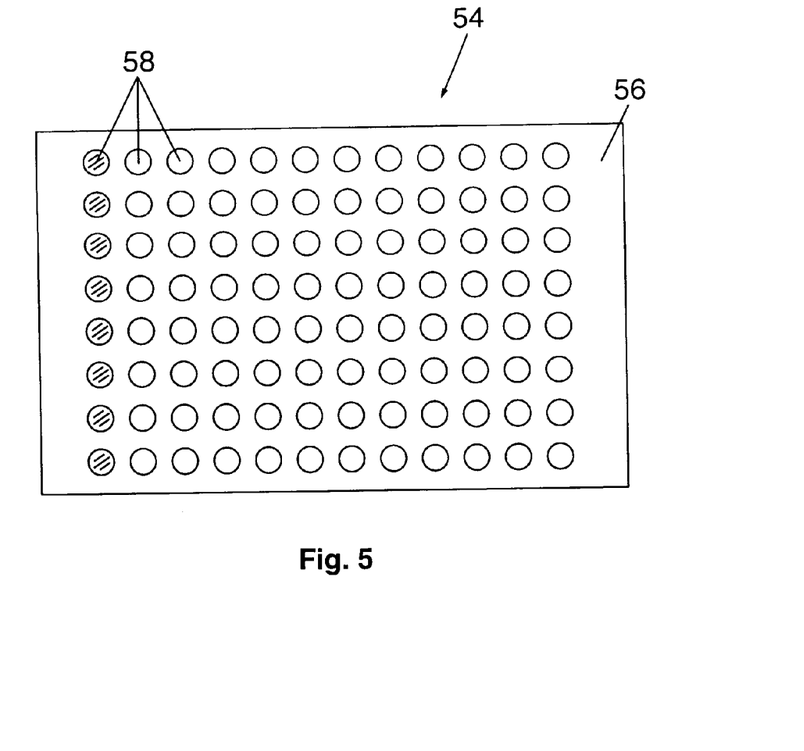
FIG. 5 is a top view of an alternative plate having opaque markers according to the invention.

Another example is illustrated in FIG. 5 which shows an alternative embodiment of a multiwell plate 54. Plate 54 comprises a plate body 56 having a plurality of wells 58 similar to the embodiment of FIG. 1. In plate 54, the bottoms of wells 58 are made to be opaque so that they will prevent the transmission of light through body 56. In this way, the bottoms of wells 58 serve as markers to prevent the transmission of light directly onto a sensor. The opaque regions may be integrally formed within wells 58 or may be included on a mask that is disposed on the bottom of the plate 54.

Figure 6:
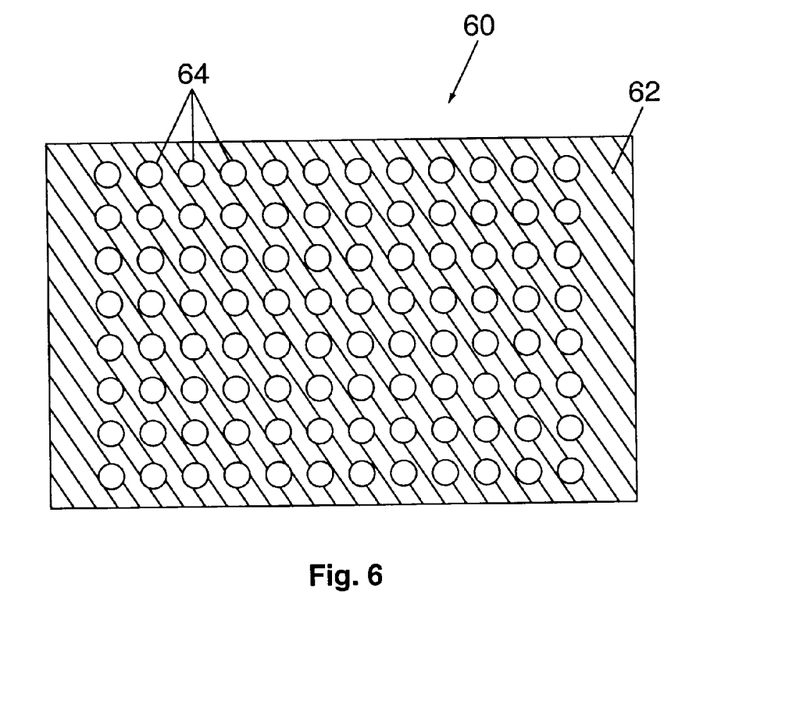
FIG. 6 is a top view of another alternative embodiment of a plate having transparent markers according to the invention.

Referring to FIG. 6, another alternative embodiment of a plate 60 will be described. Plate 60 comprises a plate body 62 having a plurality of wells 64 similar to previous embodiments. Plate body 62 is constructed such that it is opaque everywhere except at wells 64. In this way, wells 64 will transmit light through plate body 62. When plate 60 is used with system 8, the controller will be configured to open the valve when the passage of light through plate 60 is detected by the sensor.

Figure 7:
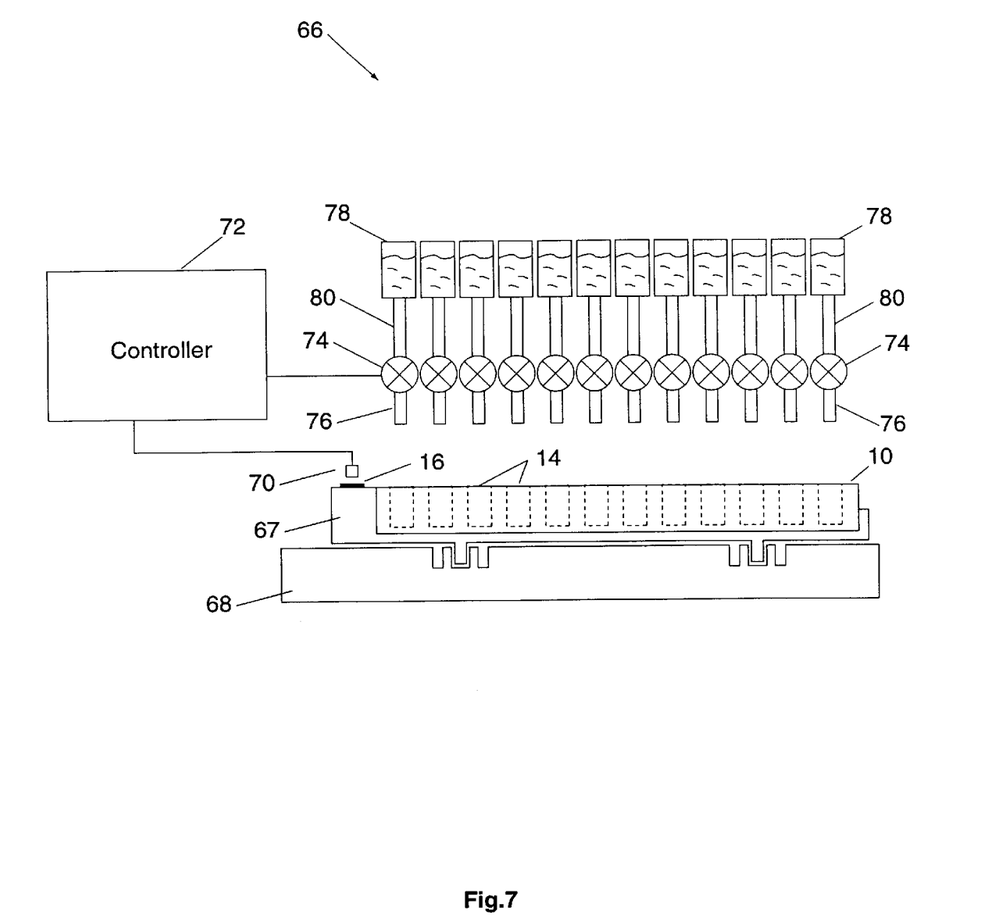
FIG. 7 is a schematic diagram of an alternative liquid dispensing system according to the invention.

Referring now to FIG. 7, an alternative embodiment of a liquid dispensing system 66 will be described. System 66 may be used with plate 10 or any of the other plates described herein. Plate 10 rests upon a carrier 67 which in turn rests on a base 68. A sensor 70 is disposed above carrier 67 similar to the embodiment of FIG. 1. Sensor 70 is coupled to a controller 72 which in turn is coupled to a plurality of valves 74. In turn, valves 74 are each connected to a dispensing element 76. Each valve 74 is also coupled to a source of liquid 78 by tubes 80.

To dispense liquid into wells 14, carrier 67 and plate 10 are advanced until the first marker 16 is sensed with sensor 70 in a manner similar to that described in connection with system 8. Controller 72 then sends a signal to open one or more of valves 74. The liquid from sources 78 (which is preferably under pressure) is then transferred through dispensing elements 76 and into wells 14. One particular advantage of the arrangement of FIG. 7 is that a separate source of liquid is used for each dispensing element 76. In this way, different types of liquids may be stored in each source so that wells 14 may be provided with a wide assortment of liquids.

The invention has now been described in detail for purposes of clarity of understanding. However, it will be appreciated that certain changes and modifications may be practiced within the scope of the appended claims. Hence, the scope and content are not limited by the foregoing but should be construed with reference to the appended claims including the full range of equivalents to which those claims are entitled.

What is claimed is:

1. A method for dispensing a liquid, comprising:

providing a plate having a plurality of wells;

providing at least one marker that is spaced apart from the wells;

moving the plate and the marker relative to a plurality of liquid dispensing elements;

sensing the presence of the marker with a non-contact sensor that is disposed at a known location relative to the dispensing elements, wherein sensing of the marker indicates that at least some of the wells are aligned with the dispensing elements; and dispensing liquid from the dispensing elements and into the aligned wells upon sensing the presence of the marker.

2. A method as in claim 1, wherein the marker is disposed on a carrier, and further comprising positioning the plate on the carrier and translating the carrier to move the plate.

3. A method as in claim 1, wherein the wells are disposed in rows, wherein a separate marker is associated with each row, and further comprising moving the plate and the markers until a second one of the markers is sensed and dispensing liquid from the dispensing elements into a second row of the wells.

4. A method as in claim 3, wherein each marker is aligned with one of the rows of wells.

5. A method as in claim 1, further comprising dispensing the same liquid from each dispensing element.

6. A method as in claim 1, further comprising dispensing a different liquid from each dispensing element.

7. A method as in claim 1, further comprising controlling the volume of liquid dispensed into the aligned wells.

8. A method as in claim 1, wherein the liquid is under pressure, and further comprising opening a valve positioned between the pressurized liquid and the dispensing elements after sensing the presence of the marker to dispense the liquid from the dispensing elements.

9. A method as in claim 1, wherein the marker comprises a transparent region in the plate, and further comprising sensing with the sensor the transmission of light through the transparent region.

10. A method as in claim 1, wherein the marker comprises an opaque region in the plate, and further comprising sensing with the sensor the blockage of light caused by the marker.

11. A method as in claim 1, further comprising sensing a change in reflected light to sense the presence of the marker.

12. A method as in claim 1, wherein the sensor is vertically aligned with the dispensing elements.

13. A liquid dispensing apparatus, comprising:
   at least one source of liquid;
   a plurality of liquid dispensing elements coupled to the source of liquid;
   a non-contact sensor disposed at a known location relative to the dispensing elements, wherein the sensor is adapted to sense the presence of a marker that is spaced apart from a plurality of wells of a plate; and
   a controller to dispense liquid from the dispensing elements upon receipt of a signal from the sensor indicating that the marker has been sensed and that at least some of the wells are aligned with the dispensing elements.

14. An apparatus as in claim 13, wherein the source of liquid is under pressure, and further comprising at least one valve coupled to the source of liquid, wherein the controller is configured to open the valve upon receipt of the signal from the sensor to allow the liquid to be dispensed through the dispensing elements.

15. An apparatus as in claim 14, wherein the controller comprises a relay which sends a signal to open the valve upon receipt of the signal from the sensor.

16. An apparatus as in claim 13, further comprising a manifold to which the dispensing elements are coupled.

17. An apparatus as in claim 13, further comprising a carrier having the marker, wherein the carrier is adapted to removably hold the plate.

18. An apparatus as in claim 17, further comprising a base having at least one track along which the carrier is translatable.

19. An apparatus as in claim 13, further comprising a plurality of liquid sources, wherein each dispensing element is coupled to a separate source of liquid.

20. An apparatus as in claim 13, wherein the sensor is vertically aligned with the dispensing elements.

21. A liquid dispensing system, comprising:
   a plate having a plurality of wells;
   a carrier having at least one marker and a region for removably holding the plate such that the marker is spaced apart from the wells;
   at least one source of liquid;
   a plurality of liquid dispensing elements coupled to the source of liquid;
   a non-contact sensor that is disposed to sense the presence of the marker when at least some of the wells are aligned with the dispensing elements; and
   a controller to dispense liquid from the dispensing elements upon receipt of a signal from the sensor indicating that the marker has been sensed and that at least some of the wells are aligned with the dispensing elements.

22. A system as in claim 21, further comprising a base having at least one track along which the carrier is translatable.

23. A system as in claim 21, wherein the marker comprises a darkened region on the carrier, and wherein the sensor is configured to sense a change in reflectance of light as the sensor passes over the marker.

24. A system as in claim 21, wherein the wells are disposed in rows and a separate marker for each row is included on the carrier.

25. A system as in claim 21, wherein the source of liquid is under pressure, and further comprising at least one valve coupled to the source of liquid, wherein the controller is configured to open the valve upon receipt of the signal from the sensor to allow the liquid to be dispensed through the dispensing elements.

26. A system as in claim 25, wherein the controller comprises a relay which sends a signal to open the valve upon receipt of the signal from the sensor.

27. A system as in claim 21, further comprising a manifold to which the dispensing elements are coupled.

28. A system as in claim 21, further comprising a plurality of liquid sources, wherein each dispensing element is coupled to a separate source of liquid.

29. A multi-well plate, comprising:
   a plate body having a plurality of wells that are arranged in rows; and
   a plurality of markers positioned on the plate body at locations spaced apart from the wells, with each marker corresponding to a separate row of wells, wherein the markers are adapted to be detected by a sensor to indicate the position of the wells relative to dispensing elements that are used to introduce a liquid into the wells.

30. A plate as in claim 29, wherein each marker comprises a transparent region in the plate that is surrounded by an opaque area.

31. A plate as in claim 29, wherein each marker comprises an opaque region in the plate that is surrounded by a transparent area.

32. A method for dispensing a liquid, comprising:
   providing a plate having a plurality of wells;
   providing at least one marker that is associated with at least some of the wells;
   moving the plate and the marker relative to a plurality of liquid dispensing elements;
   sensing the presence of the marker with a sensor that is disposed at a known location relative to the dispensing elements, wherein sensing of the marker indicates that at least some of the wells are aligned with the dispensing elements; and
   dispensing liquid from the dispensing elements and into the aligned wells after sensing the presence of the marker;
   wherein the marker comprises a transparent region in the plate, and further comprising sensing with the sensor the transmission of light through the transparent region.

33. A method for dispensing a liquid, comprising:

providing a plate having a plurality of wells;

providing at least one marker that is associated with at least some of the wells;

moving the plate and the marker relative to a plurality of liquid dispensing elements;

sensing the presence of the marker with a sensor that is disposed at a known location relative to the dispensing elements, wherein sensing of the marker indicates that at least some of the wells are aligned with the dispensing elements; and dispensing liquid from the dispensing elements and into the aligned wells after sensing the presence of the marker;

wherein the marker comprises an opaque region in the plate, and further comprising sensing with the sensor the blockage of light caused by the marker.

34. A liquid dispensing system, comprising:

a plate having a plurality of wells;

a carrier having at least one marker and a region for removably holding the plate;

at least one source of liquid;

a plurality of liquid dispensing elements coupled to the source of liquid;

a sensor that is disposed to sense the presence of the marker when at least some of the wells are aligned with the dispensing elements; and a controller to dispense liquid from the dispensing elements upon receipt of a signal from the sensor indicating that the marker has been sensed and that at least some of the wells are aligned with the dispensing elements;

wherein the marker comprises a darkened region on the carrier, and wherein the sensor is configured to sense a change in reflectance of light as the sensor passes over the marker.

35. A multi-well plate, comprising:

a plate body having a plurality of wells; and at least one marker selectively positioned on the plate body, wherein the marker is adapted to be detected by a sensor to indicate the position of the wells relative to dispensing elements that are used to introduce a liquid into the wells;

wherein the marker comprises a transparent region in the plate that is surrounded by an opaque area.

36. A multi-well plate, comprising:

a plate body having a plurality of wells; and at least one marker selectively positioned on the plate body, wherein the marker is adapted to be detected by a sensor to indicate the position of the wells relative to dispensing elements that are used to introduce a liquid into the wells;

wherein the marker comprises an opaque region in the plate that is surrounded by a transparent area.

* * * * *